United States Patent [19]
Bacher et al.

[11] Patent Number: 5,599,307
[45] Date of Patent: Feb. 4, 1997

[54] CATHETER AND METHOD FOR THE PREVENTION AND/OR TREATMENT OF STENOTIC PROCESSES OF VESSELS AND CAVITIES

[75] Inventors: Peter Bacher, Nürnberg, Germany; Jeanine M. Walenga, Lombard, Ill.

[73] Assignee: Loyola University of Chicago, Chicago, Ill.

[21] Appl. No.: 537,033

[22] Filed: Sep. 29, 1995

Related U.S. Application Data

[63] Continuation of Ser. No. 97,653, Jul. 26, 1993, abandoned.

[51] Int. Cl.⁶ .................................................. A61M 29/00
[52] U.S. Cl. .......................... 604/101; 606/194; 604/265; 604/53; 623/12
[58] Field of Search ........................... 604/96, 101, 265, 604/53, 56, 280; 606/191, 192, 194; 623/1, 11, 12

[56] References Cited

U.S. PATENT DOCUMENTS

| | | | |
|---|---|---|---|
| 4,417,576 | 11/1983 | Baran | 604/101 |
| 4,610,662 | 9/1986 | Weikl | 604/101 |
| 4,636,195 | 1/1987 | Wolinsky | 604/101 |
| 4,824,436 | 4/1989 | Wolinsky | 604/53 |
| 5,087,244 | 2/1992 | Wolinsky et al. | 604/53 |
| 5,092,841 | 3/1992 | Spears | 604/96 |
| 5,100,429 | 3/1992 | Sinofsky et al. | 606/195 |
| 5,116,318 | 5/1992 | Hillstead | 604/96 |
| 5,135,484 | 8/1992 | Wright | 604/101 |
| 5,180,366 | 1/1993 | Woods | 604/96 |
| 5,199,951 | 4/1993 | Spears | 604/96 |
| 5,222,941 | 6/1993 | Don Michael | 604/101 |
| 5,240,913 | 8/1993 | Maraganore et al. | 514/13 |
| 5,246,437 | 9/1993 | Abela | 606/5 |
| 5,250,519 | 10/1993 | Conrad | 514/56 |
| 5,256,141 | 10/1993 | Gencheff et al. | 604/53 |
| 5,279,565 | 1/1994 | Klein | 604/105 |
| 5,308,622 | 5/1994 | Casscells et al. | 424/422 |
| 5,314,409 | 5/1994 | Sarosiek et al. | 604/101 |
| 5,318,531 | 6/1994 | Leone | 604/96 |
| 5,320,604 | 6/1994 | Walker et al. | 604/101 |

OTHER PUBLICATIONS

Stedman's Medical Dictionary, 25th Edition, published by Williams & Wilkins, pp. 157, 711, 712, 722, 723.

*Primary Examiner*—Randall L. Green
*Assistant Examiner*—Chalin Smith
*Attorney, Agent, or Firm*—Marshall, O'Toole, Gerstein, Murray & Borun

[57] ABSTRACT

A catheter for preventing the stenosis or restenosis of a body vessel or cavity, e.g., a blood vessel, whereby a membrane may be applied to the inner surface of the vessel or cavity. The inventive catheter tip utilizes (a) two inflatable chamber balloons which, when inflated, isolate a portion of the vessel or cavity for treatment and (b) an inflatable treatment balloon disposed between the two chamber balloons which provides a means for treating the isolated site. The invention permits the flow of body fluid, e.g., blood, to the distal side of the catheter tip while the balloons are in an inflated state. The invention further permits the rinsing and flushing of fluids or medications of an isolated longitudinal portion of the vessel or cavity prior to and after an application of a membrane located on the treatment balloon. The invention is useful for the prevention of restenosis of a blood vessel after PTA, PTCA or atherectomy or like procedures, or more generally for the treatment of any cavity requiring a membrane, film or coating.

44 Claims, 4 Drawing Sheets

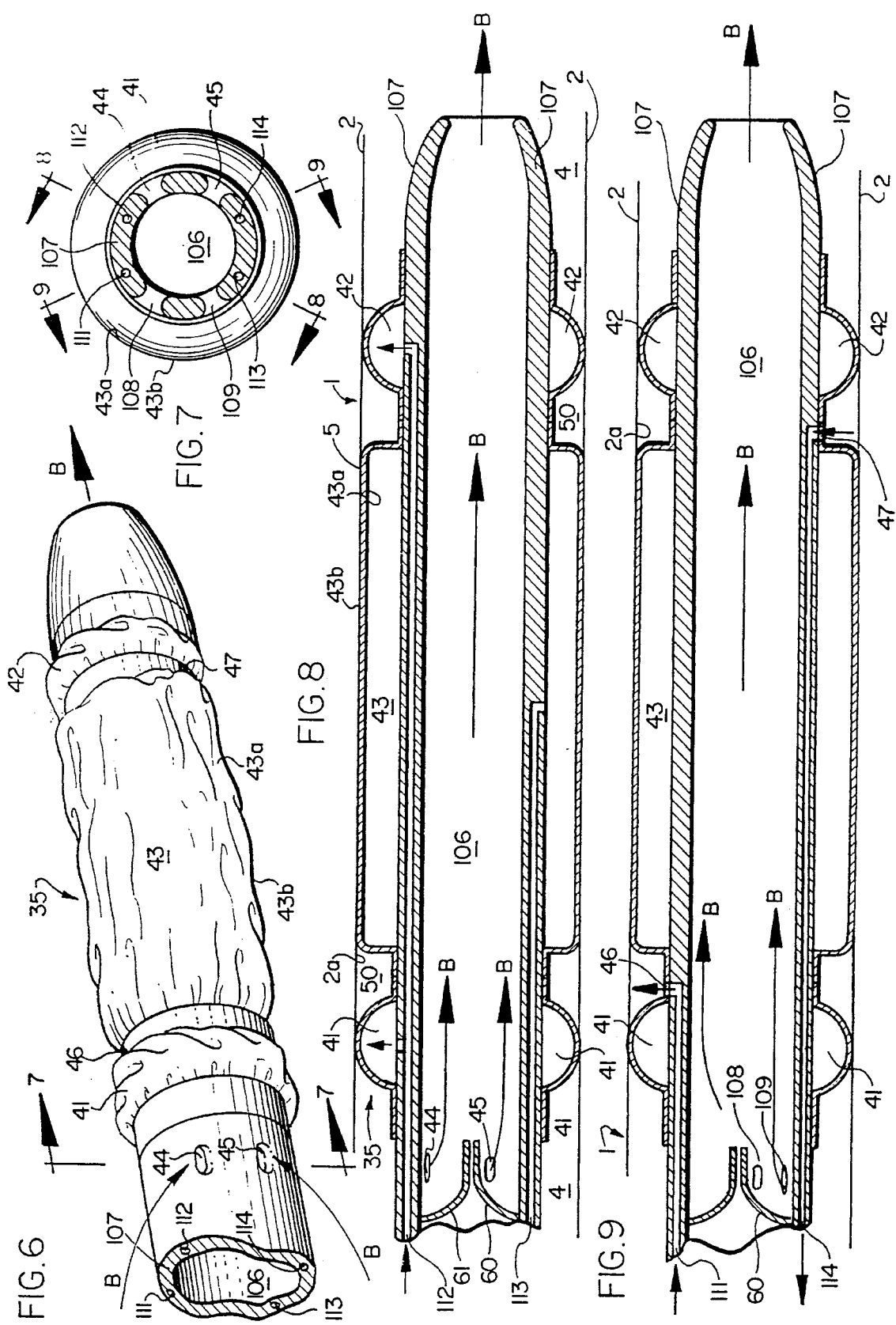

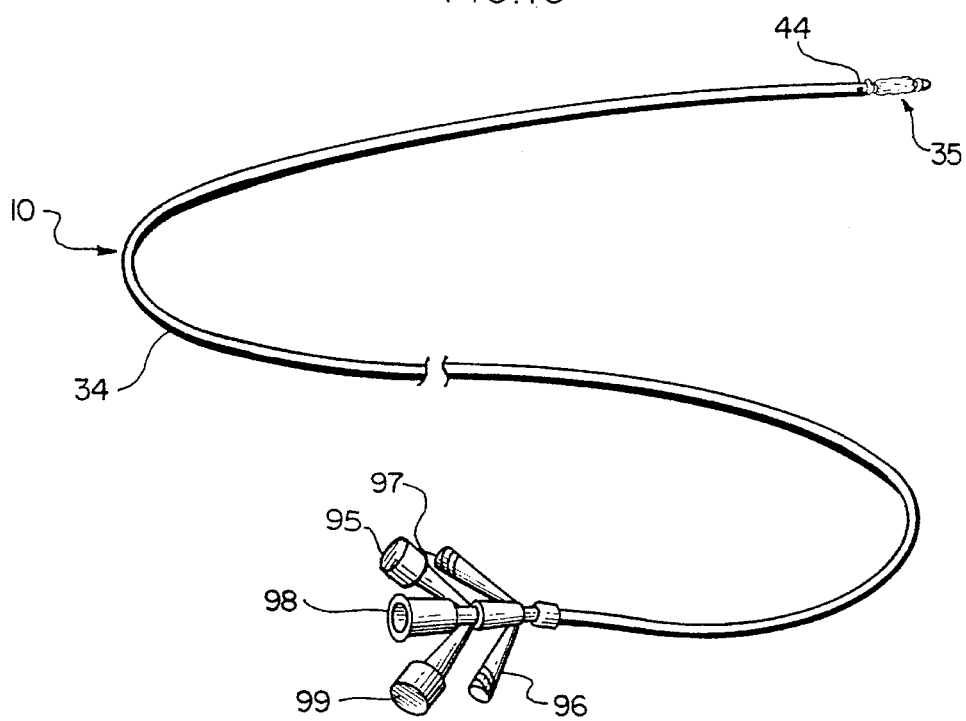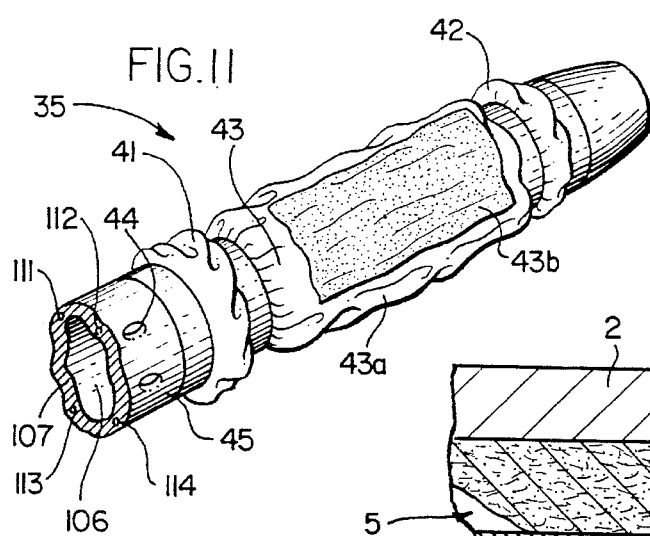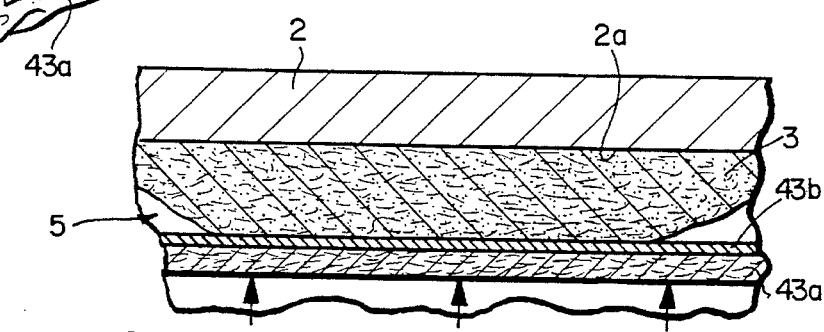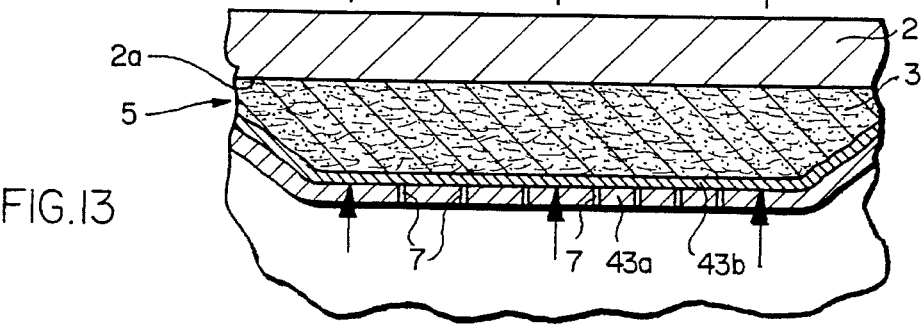

CATHETER AND METHOD FOR THE PREVENTION AND/OR TREATMENT OF STENOTIC PROCESSES OF VESSELS AND CAVITIES

This is a continuation of U.S. application Ser. No. 08/097,653, filed July. 26, 1993, now abandoned.

FIELD OF THE INVENTION

The invention disclosed and claimed herein relates generally to a system for the treatment of the walls of a body vessel or cavity, and more particularly to the prevention of stenosis or restenosis of a blood vessel. The invention further relates to a device for use in treatment of sites where angioplasty or atherectomy has been performed.

BACKGROUND OF THE INVENTION

For various reasons, e.g., vessel wall narrowing caused by various diseases, it sometimes becomes necessary to treat the lumen of vessels or cavities which carry body fluids, for example, blood vessels. The present invention is directed to the prophylaxis of problems which may occur as a result of such treatments and diseases.

For example, treatment may be necessary to cure the effects of arteriosclerosis, a degenerative disease in which atheromatous plaques cause the stenosis, or narrowing, of a human blood vessel such as an artery or vein. Atheromatous plaques may comprise, for example, any of the following, including combinations thereof: lipids or other fatty matter, fibrous materials, calcium, blood cells, collagen or other thrombotic deposits. An area of atheromatous plaque located on an artery wall is known as a "lesion".

Briefly, atheromatous plaque, which has the ability to ultimately result in the formation of a lesion, may begin developing by the accumulation of lipid-laden cells in the intimal layer of the artery wall. Examples of lipid-laden cells which are found in the circulating blood include monocytes and macrophages. An accumulation of such lipid-laden cells in the intimal layer of the artery wall may become likely when lipid-laden cells adhere to the endothelial layer of the artery wall. Once the lipid-laden cells or lipid vesicles are present in the endothelial layer, lipids are highly susceptible to passing through the endothelial cells to the intima. A lesion may be formed upon further continuation of this process.

In instances when stenosis caused by atheromatous plaque reduces blood flow through an artery, the tissue or organ distal to the stenosis fails to receive an adequate blood supply, thereby severely compromising such tissue or organ. An acute lapse in the blood supply to the brain (a stroke) or heart (a heart attack) can be fatal or cause severe tissue damage. Further, other disfunctions of organ physiology can be caused by chronic processes which are related to stenotic lesions. As a result, special procedures have been developed to combat stenosis of commonly affected arteries such as the aorta, iliac, femoral, coronary and cerebral arteries.

Although bypass surgery, such as coronary artery bypass surgery, is often used to repair damaged and blocked portions of arteries, percutaneous transluminal angioplasty ("PTA") and percutaneous transluminal coronary angioplasty ("PTCA") have been developed as an alternative to bypass surgery in order to repair blocked or partially blocked arteries. Since the introduction of PTA and PTCA, also known as "balloon angioplasty," these techniques have been performed in millions of patients for the treatment of arterial stenosis.

Certain other procedures have also been developed to repair blocked or partially blocked arteries. An example of such a further procedure is atherectomy, in which a rotating blade located on the distal tip of a catheter is placed at the site of a lesion. The rotating blade serves to reduce the size of the lesion by shearing plaque off the arterial wall. Another procedure developed to repair blocked or partially blocked body vessels (e.g., arteries) uses a laser-equipped catheter, in which a laser located on the distal tip of a catheter is placed at or near the site of a lesion. The laser serves to reduce the size of the lesion by shearing plaque off the arterial wall. Stent implantation and slurry treatments are further examples of recently developed procedures for the treatment of blocked arteries.

In many instances, however, treatment of the body vessel or cavity by one of the above-described procedures is not entirely satisfactory because the surgical procedure may damage, traumatize or incompletely treat the vessel or cavity. In relation to blood vessels, due to various factors, some of which are incompletely understood, clinically relevant restenosis (the reappearance of stenosis) has been found to occur in up to 50% of patients who had received PTA and PTCA treatments.

Restenosis may occur, for example, as a result of the damage and trauma caused to vessel walls by the high balloon pressure which is used in PTA and PTCA procedures. For example, when trauma denudes the vessel wall of endothelial cells, exposing the inner layers of cells to flowing blood, various mechanisms (e.g., repair mechanisms such as smooth muscle cell proliferation and migration) may lead to restenosis of the vessel. Therefore, one goal of a treatment for preventing restenosis of a blood vessel is to prevent exposure of the inner tissue layers of the artery wall to blood. As a general matter, it will usually be desirable to prevent the exposure of the inner layers of any afflicted (e.g., diseased) portion of a body vessel or cavity to the body fluid which is found therein.

Restenosis may also result from the portion of plaque which will generally remain on the artery wall even after a procedure such as balloon angioplasty has been performed on a lesion. Endothelial cells cover the surface of blood vessels and render the surface non-thrombogenic and non-reactive. Where plaque remains on the artery wall, this portion of the artery wall lacks the protection provided by the endothelial cells. Therefore, further plaque is likely to build up on the plaque which remains after the angioplasty procedure.

A still further cause of restenosis is that, as a result of the body's immune response, white blood cells may attach themselves to any plaque or damaged arterial wall which persists after one of the above-described procedures has been performed. After these white blood cells attach to this area, further plaque may easily build up.

The danger of restenosis generally also exists after the use of the non-balloon procedures (atherectomy and laser-equipped catheters) mentioned above. These procedures have several disadvantages, including the danger that if the laser or the cutting blade is not properly oriented in use, damage to the vessel wall may result. Such damage may have a high probability of leading to restenosis for the reasons described above.

Stent implantation (such as that described in U.S. Pat. No. 5,100,429 to Sinofsky et al.), which shields a lesion and provides structural support, is generally undesirable because the procedure will narrow the vessel opening at the stent location and introduce a foreign body into the vessel which itself is likely to promote stenosis. Foreign bodies are both subject to (a) attack by white blood cells, leading to the dangers discussed above, and (b) promoting the formation of a thrombus. Thrombotic particles are likely to build up at the endpoints of the stent.

Therefore, any treatment of the vessel which has the possibility of damaging or causing trauma to the vessel, including surgery, PTA, PTCA, atherectomy, laser and slurry treatments, may lead to restenosis.

Accordingly, where a body vessel or cavity has been treated to relieve a disorder such as a blockage, it is desirable to have the ability to further treat that site to overcome the problems discussed above. For example, it is desirable to further treat the site of an angioplasty procedure in order to prevent restenosis of the artery.

It is also desirable that, during such further treatment, blood or other body fluid be supplied to the distal side of the site of treatment, e.g., so that downstream tissues are not deprived of oxygen and other nutrients supplied by the blood. This will also enable the body to carry on its normal functions during the procedure.

It is also desirable that such further treatment include the ability to isolate the treatment site from the flow of the body fluid (e.g., blood). In this manner, the site may be treated without interference by the body fluid. Where the treatment site is isolated it is also desirable to have the ability (a) to rinse and flush the isolated site to prepare the vessel or cavity walls (e.g., arterial walls) for this further treatment, (b) to dispense medication and (c) to protect the vessel or cavity wall, for example, from mediators which may cause restenosis after PTA, PTCA or atherectomy.

SUMMARY OF THE INVENTION

The invention disclosed and claimed herein serves to overcome, reduce or otherwise obviate the above-described problems presently encountered when treating body vessels. The invention also may be utilized to aid in the prevention of restenosis of blood vessels.

Briefly, the invention comprises a catheter having an improved catheter tip useful for the treatment of the walls of a body vessel or cavity. The invention additionally provides a method for the prevention of stenosis of a body vessel or cavity. The catheter tip and method of the present invention also relate to the treatment of sites where angioplasty or atherectomy previously has been performed on an artery or blood vessel. The treatment is useful in preventing restenosis of a vessel without the need for surgical intervention.

In one aspect, the invention comprises a catheter which includes an elongated flexible shaft. Located at the outer or distal end of the shaft is a catheter tip which preferably comprises (a) two spaced inflatable chamber balloons mounted on the catheter tip and (b) a third, inflatable treatment balloon, preferably made of a porous material, also mounted on the catheter tip and disposed between the spaced chamber balloons. A releasable coating or membrane, preferably having a structure substantially similar to the physiological structure of the wall of the vessel or cavity (e.g., the endothelial layer of a blood vessel), is preferably disposed on the wall surface of the treatment balloon. Alternatively, the membrane or film may be generated at the treatment site by dispensing a membrane material comprising a slurry, solution or other fluid, followed by solidification of the fluid at the treatment site.

The catheter tip is inserted into a body vessel or cavity and directed to a desired location, for example to the location of a lesion on the wall of a blood vessel. The area to be treated, e.g., a lesion or a damaged portion of a body vessel, is placed between the chamber balloons. The two spaced chamber balloons are inflated thereby forming a chamber which isolates a portion of the vessel between the inflated balloons.

Subsequent to inflating the spaced chamber balloons, the treatment balloon is inflated with pressure provided by a pressurizing fluid or medium. The pressurizing fluid forces the outer wall of the treatment balloon to come in intimate contact with the vessel wall surface. Due to the relatively high inflating pressure on the vessel wall surface, a releasable membrane material, which is disposed on the outer wall of the treatment balloon, is removed or separated from the balloon surface. The membrane forms, adheres or attaches as a film, coating, layer or membrane on the surface of the vessel wall.

Additionally, because the treatment balloon preferably has a porous outer surface, pressurized inflation fluid and/or medication may be dispensed through the pores to form a fluid layer between the treatment balloon surface and the membrane. This fluid layer preferably facilitates the release of the membrane from the outer surface of the treatment balloon. While the treatment balloon need not have such a porous outer surface, such a feature is preferable because it serves to aid in the transfer of the film or membrane to the surface of the vessel wall.

According to a further feature of the invention, prior to inflating the treatment balloon, the body fluid (e.g., blood) is evacuated from the chamber formed by the inflated, spaced chamber balloons. For this purpose, openings or outlets are preferably placed in the wall of the catheter tip at a location between the two spaced chamber balloons. These openings or outlets are connected to conduits (preferably located in the catheter shaft) which travel to the proximal end of the catheter shaft (i.e., lead to the outside of the body). Following evacuation, the wall of the vessel in the chamber formed by the spaced chamber balloons is preferably prepared for transfer of the film or membrane from the treatment balloon to the vessel wall. This preparation begins by first flushing the chamber with a desired medicated preparation prior to inflation of the treatment balloon. After flushing takes place, the treatment balloon is inflated and the membrane is transferred to the surface of the vessel wall. While such a flushing procedure is preferable, it not required in all instances. It is contemplated that the conduits and treatment balloon may be pre-filled or pre-manufactured with a fluid before the procedure is carried out to avoid gas contact with the vessel wall.

According to another feature of the invention, the catheter is provided with a lumen, preferably located in the interior of the catheter shaft, which extends through the interior of the catheter tip to the end of the catheter tip. This lumen is provided with at least one entry hole or opening at a location proximal to the catheter tip. The entry hole or opening serves to allow body fluid such as blood to enter the lumen. The body fluid travels inside the lumen and continues downstream through the end of the catheter tip, where the body fluid is supplied downstream of the catheter tip. With this feature, blood can be supplied to tissue distal to the catheter tip when the catheter balloons are in an inflated condition.

Following the inflating procedures, the treatment balloon and spaced chamber balloons are deflated and the catheter removed from the treatment site. The membrane transferred to the vessel wall surface remains substantially in place affixed to the vessel wall.

BRIEF DESCRIPTION OF THE DRAWINGS

The invention will be better understood from the following detailed description taken in conjunction with the accompanying figures of the drawings, wherein:

FIG. 6 shows a perspective view of the catheter tip of the present invention in a deflated condition;

FIG. 7 shows a cross section view taken along lines 7—7 in FIG. 6 illustrating an embodiment of conduits ill the catheter wall;

FIG. 8 shows a longitudinal cross section view of the embodiment of the catheter tip taken along lines 8—8 in FIG. 7;

FIG. 9 shows a longitudinal cross section view of the embodiment of the catheter tip taken along lines 9—9 in FIG. 7;

FIG. 10 shows a perspective view of an embodiment of an elongated flexible catheter shaft and catheter tip of the present invention;

FIG. 11 shows a perspective view of the catheter tip of the present invention in a deflated state;

FIG. 12 shows a fragmentary, cross section view of the artery of FIG. 2 with the treatment balloon in a semi-inflated state;

FIG. 13 shows the artery and treatment balloon of FIG. 12 wherein the treatment balloon is illustrated in a substantially completely inflated state;

DETAILED DESCRIPTION

Figure 1:
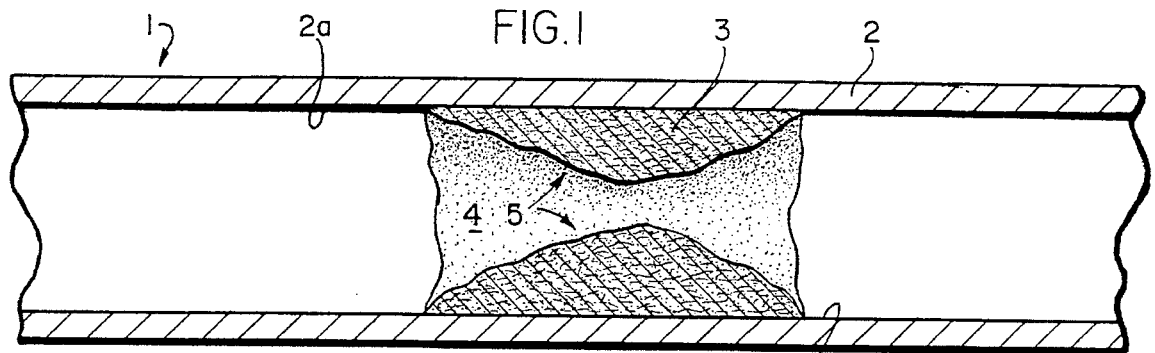
FIG. 1 shows a fragmentary, longitudinal cross section view of an artery having a lesion thereon.
Figure 2:
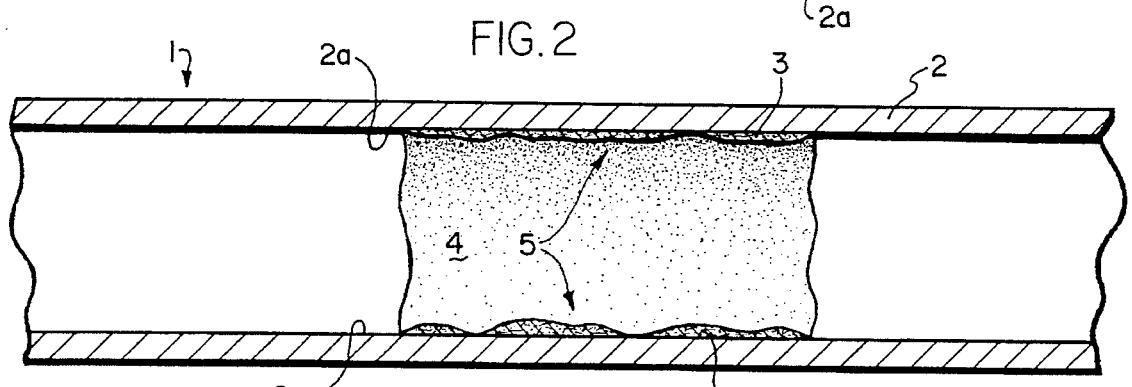
FIG. 2 shows a fragmentary, longitudinal cross section view of an artery, having a lesion thereon which has been treated by a PTA, PTCA or atherectomy procedure.

The drawings show various views of an embodiment of a catheter tip of the present invention which is useful in the treatment of the walls of a body vessel or cavity, such as the blood vessel shown in FIGS. 1 and 2. Like elements in the various figures of the drawings are designated with like numerals. However, it should be understood that although this description may refer to use of the catheter tip for the prevention of restenosis of a blood vessel (e.g., an artery or a vein), the inventive catheter and method may be used to treat the walls of any body vessel or cavity. By way of example only, the inventive catheter and method may also be used to treat the large and small intestines, the renal system, the liver system, and the stomach. Further, the inventive catheter and treatment may be utilized in conjunction with treatments for any of the following disorders which commonly afflict body vessels or cavities: infection, tumors, ulcers, inflammation, disease or blockages.

A blood vessel requiring treatment due to a partial occlusion by plaque will first be described with reference to FIGS. 1 and 2. Although a procedure such as PTA, PTCA or atherectomy is not necessarily performed before the inventive procedure, such a procedure is preferably performed so that the occlusion of the blood vessel is at least partially relieved. Use of the inventive catheter and method, however, is not limited to treatments following a PTA, PTCA or atherectomy procedure. Alternatively, the catheter tip of the present invention may be adapted to perform both (a) a conventional PTA or PTCA procedure and (b) the inventive treatment described in detail below.

FIG. 1 shows a cross section of a partially occluded blood vessel, such as an artery 1, prior to any treatment of the vessel. A body of atheromatous plaque 3 is shown accumulated on an inner surface 2a of artery wall 2. Plaque 3 extends into lumen 4 of the artery defined by artery wall 2 and forms an area known as a lesion 5 which extends along a portion of the vessel wall as seen in FIG. 1 and serves to partially occlude or constrict lumen 4.

FIG. 2 shows a cross section of the partially occluded blood vessel or artery 1 shown in FIG. 1; however, the artery has been treated to at least partially relieve the occlusion, such as by a conventional balloon angioplasty procedure. As described above, the balloon angioplasty procedure compresses plaque 3 against artery wall 2. Nevertheless, even after the procedure, a body of plaque 3 in the form of lesion 5 remains attached to the inner surface 2a of artery wall 2, although the blockage of lumen 4 has been reduced by the balloon angioplasty procedure. Further, procedures such as PTA or PTCA may cause one or more of the problems heretofore described, thereby resulting in the danger of restenosis of the artery. It is therefore highly desirable to further treat the artery 1 in order to prevent restenosis of the artery 1.

Referring next to FIG. 10, an embodiment of a catheter in accordance with the invention is shown. The catheter is referred to generally as element 10. Catheter tip 35 is attached, by any suitable means, at or near the end of an elongated, flexible catheter shaft 34. Attached to catheter shaft 34 are inlet ports 95, 96, 97, 98 and 99 which are adapted for the insertion of devices which supply necessary, preferred or desired materials to catheter tip 35. Inlet ports 95, 96, 97, 98 and 99 are preferably attached via openings (not shown) at or near the end of catheter shaft 34 to conduits which travel along the length of flexible catheter shaft 34 to allow various materials (such as flushing material, medication and pressurizing fluids, all of which are described below in greater detail) to be supplied to or removed from catheter tip 35. For example, inlets 95–99 may be connected with conduits 106, 111–114 shown in FIGS. 6–9, described below in greater detail.

Catheter tip 35 is shown in greater detail in FIG. 6. Catheter tip 35 includes inflatable chamber balloon 41 and inflatable chamber balloon 42, each of which is attached by any suitable means at or near an end of catheter tip 35. Each chamber balloon 41 and 42 is inflatable so that upon filling a chamber balloon with a fluid (e.g., a liquid such as saline solution or a gas), the balloon expands to contact the wall of the artery into which catheter tip 35 is inserted. Such a fluid used to inflate a catheter balloon is referred to herein as a pressurizing fluid or medium. Chamber balloons 41, 42 are maintained under sufficient pressure so that the contact between the artery wall and balloon surface is adequate to prevent passage of blood and other liquids from one side of the inflated chamber balloon to the other side of the inflated balloon (i.e., upstream or downstream of the chamber balloon). Inflation of spaced chamber balloons 41, 42 inside an artery defines a chamber 50 (see FIG. 8), or isolated longitudinal portion of the artery between the spaced balloons. The damaged portion of an artery wall may be isolated and treated inside of isolated chamber 50.

Catheter tip 35 also includes an inflatable treatment balloon 43 located between chamber balloons 41, 42. Treatment balloon 43 is provided on its exterior wall 43a with a releasable coating, membrane or film 43b. The material comprising element 43b will generally be referred to herein as membrane 43b. In the instance of a blood vessel, membrane 43b preferably comprises a material which has a structure substantially similar to the physiological structure of the surface of the walls of the blood vessel into which the catheter tip 35 has been inserted. The material forming membrane 43b may be, for example, similar to the endothelial cells found on the inner surface of an artery wall, and may comprise inverted homologues, homologues, heterologues, or autologues of endothelial cells. Further, the endothelial cells referred to in the preceding sentence may be denaturalized endothelial cells and need not be human endothelial cells. Still further, the material forming membrane 43b may also comprise a material which is not naturally found in the endothelium. It is appreciated that the material comprising membrane 43b may also be suitable to provide treatment (e.g., as a medication) for different diseases such as tumors, inflammation or ulcers. Membrane 43b may also comprise material which is able to release a local drug for the treatment of the above-described disorders, including stenotic processes.

Releasable membrane 43b is optionally temporarily held on the wall 43a with a material which acts like a "glue", for example a sugar which can be dissolved upon hydration at the treatment site. Alternatively, prior to the procedure, membrane 43b may be placed on the wall 43a and then shrunk onto the balloon 43 to secure the membrane 43b onto wall 43a. For example, membrane 43b may be placed on wall 43a and then heated to remove moisture, thereby shrinking membrane 43b onto wall 43a.

Preferably, when in a deflated state, all of the above-described balloons on catheter tip 35 are disposed below the level of the outer surface of catheter wall 107 (i.e., the balloons have a cross section having a diameter which is less than or equal to the diameter of the body of the catheter tip). For example, balloons 41–43 may be housed within a depression in catheter wall 107. This feature will preferably provide the catheter tip with a smooth outer surface, thereby preferably avoiding vessel damage during insertion and movement of the catheter tip to the treatment site. This feature will also preferably serve to protect the releasable membrane 43b disposed on the surface of the treatment balloon 43. Alternatively, a cover may be provided over the treatment balloon which may be removed prior to the inventive procedure, which is described below in detail.

Treatment balloon 43, which is shown in an uninflated state in FIG. 6, is inflatable preferably to an extent that balloon 43 provides pressure against the artery wall sufficient to permit transfer of releasable membrane 43b from the outside wall surface 43a of treatment balloon 43 to the corresponding inner wall surface of a vessel or cavity. For example, FIGS. 5, 12 and 13 (which will be discussed below in greater detail) show the membrane 43b positioned against the inner surface 2a of artery wall 2 and/or against lesion 5. It should be understood that membrane 43b will preferably cover both lesion 5 and a portion of exposed wall surface 2a. It is contemplated that a pressure of less than about 10–13 atmospheres (typically used for balloon angioplasty), for example in the range of about 1–8 atmospheres, and preferably about 3–5 atmospheres, would be useful with the invention. The amount of pressure necessary may be determined by viewing the treatment site on an x-ray screen during a catheter installation procedure. A marker may be used on the treatment balloon and/or membrane which is placed on the treatment balloon (described in detail below). It is understood that the pressure which may be used is completely variable and may depend, for example, upon the vessel in which the catheter tip is inserted and the characteristics of the membrane which is selected for use.

Although membrane 43b may be applied as a solid layer of material on the balloon wall surface 43a, the material forming membrane 43b may be delivered to the treatment site as a fluid (e.g., a slurry, solution, medication or liquid) which will then be substantially solidified during a subsequent solidification step. In other words, the membrane may be generated at the treatment site. For example, two or more components, which will eventually form the membrane or film, may be provided via an inlet 46 into a chamber 50 formed by chamber balloons 41, 42 (as shown in FIG. 9); the two components may be selected so that they will react to coagulate, precipitate or otherwise mix to solidify in chamber 50, optionally with the aid of pressure from treatment balloon 43. Alternatively, after inflation of treatment balloon 43, a slurry, one example being human endothelial cells in heparin, may be dispensed onto the inner surface of artery wall 2 via inlet 46. The slurry, solution, medication or liquid provided to chamber 50 might be solidified, for example, by applying (a) localized temperature changes or (b) a chemical to change the molecular configuration of the slurry, solution, medication or liquid. It is further contemplated that such a fluid might be applied via a treatment balloon 43 which has a porous outer wall 43a, as is further described below in detail.

The membrane 43b is preferably thin enough so that it will not adversely influence the blood flow through a blood vessel. For example, the membrane preferably will not adversely influence the blood flow through a blood vessel having a diameter of about 2.0 to about 2.5 mm. Although the invention is not limited to such a thickness, the thickness of the treatment membrane 43b is contemplated to be at least about 0.2 micrometers (the approximate thickness of a single layer of endothelial cells) or thicker. It is further contemplated that the membrane thickness would preferably be in the range of about 0.2 to 1.0 micrometers.

Membrane 43b may be applied to provide any desired size or shape depending upon the type of treatment required. For example, in some cases, such as seen in FIG. 6, the membrane 43b will cover all or substantially all of the entire circumference of treatment balloon 43 prior to application of the membrane 43b. In other instances, it may be desirable to utilize a membrane 43b which does not cover the entire circumference of the treatment balloon, such as in the embodiment illustrated in FIG. 11. In the embodiment illustrated in FIG. 11, membrane 43b covers only a defined portion of treatment balloon 43. The catheter shown in the embodiment of FIG. 11 may be especially useful, for example, in treating stomach ulcers, where it may sometimes be desirable to cover only a small portion of the inner surface of the stomach wall with membrane 43b. It is recognized that although membrane 43b is shown as having a rectangular shape in FIG. 11, this need not always be the case.

As shown in FIGS. 14–17, the shape of the membrane 43b may be adapted for the treatment of body vessels, e.g., arteries, having various configurations. FIG. 14(a) illustrates a partially occluded, unbranched artery 1 similar to that shown in FIG. 1 (described above), along with a membrane suitable for the treatment thereof (FIG. 14(b)). FIG. 15(a) shows a branched artery 1 wherein plaque 3 is located on the artery wall 2 of artery 1 at locations both distal and proximal to the intersection of artery 1 and artery 1a, along with a membrane 43b adapted for the treatment thereof (FIG. 15(b)). FIG. 16(a) (where the arrow indicates the direction of blood flow) illustrates a branched artery 1 wherein plaque 3 is located only proximal to artery 1a on the side of artery 1 which intersects with artery 1a. The membrane 43b in FIG. 16(b) is adapted to cover the plaque while avoiding blockage of the intersection of artery 1 and artery 1a. FIG. 17(a) (where the arrow indicates the direction of blood flow) illustrates a branched artery 1 wherein plaque 3 is located on artery wall 2, however plaque 3 is only located distal to artery 1a on the side of artery 1 which intersects with artery 1a. The membrane 43b in FIG. 17(b) is adapted to cover the plaque while avoiding blockage of artery 1 and artery 1a. A marker, preferably viewable on an x-ray machine, is preferably placed on the membrane 43b when it is desired to place the membrane at a specific orientation with respect to the artery wall 2, such as in the case of the membranes shown in FIGS. 15–17.

Referring again to FIG. 6, treatment balloon 43 preferably includes a feature for facilitating the transfer of the above-described membrane 43b from treatment balloon wall surface 43a to the inner surface of artery wall 2. According to one embodiment of this feature of the invention, balloon wall 43a is formed of a porous material (i.e., very small or minute pinholes or openings 7 are disposed in wall surface 43a) through which a fluid (including, but not limited to, a slurry, a solution or a liquid) may be dispensed to form a fluid layer between balloon wall surface 43a and the inner surface of the membrane 43b. The fluid preferably will be dispensed after balloon 43 has been inflated and sufficient fluid pressure is supplied to balloon 43 so that fluid is forced through the pores of balloon wall 43a. The fluid pressure in the porous treatment balloon 43 prevents any liquid outside the balloon from entering treatment balloon 43 through the pores or pinholes, while at the same time the fluid pressure forces fluid to exit the treatment balloon 43 through the minute pores 7. The wall surface is preferably provided with suitable openings so that the fluid travels in only one direction, i.e., outward, from the interior of balloon 43 outside into the treatment chamber. It is optional to provide the treatment balloon 43 with pores. The size of the pores of the treatment balloon 43 is contemplated to be about 1 to about 5 micrometers in diameter if membrane 43b comprises endothelial cells. If no endothelial cells are used, the pore size can be larger.

As the fluid exits the balloon chamber, it forms a fluid layer between the balloon chamber wall surface 43a and the membrane 43b. The fluid layer generally comprises the material used to inflate treatment balloon 43 (i.e., the same pressurizing fluid or medium which is utilized to inflate treatment balloon 43 may comprise the fluid layer utilized to facilitate the transfer of membrane 43b). The fluid layer also preferably has characteristics (e.g., the ability to provide a "slippery" surface) which will aid in releasing membrane 43b from the outer balloon surface 43a. Useful fluid layers may comprise any of the following, including mixtures thereof: heparin, glycosaminoglycans, thrombin inhibitors, antiproliferative agents, growth factor inhibitors or regulators, cell function regulators, collagen, chemotherapeutics and anti-inflammatory agents.

Further, as stated above, the porous treatment balloon 43 of this feature of the invention may also be utilized to dispense a fluid (e.g., a slurry, solution, medication or liquid) comprising membrane material onto the balloon surface 2a to generate the membrane at the treatment site. After the fluid which is dispensed from treatment balloon 43 solidifies, it forms a membrane 43b and adheres to a lesion or vessel wall surface.

As shown in FIGS. 12 and 13, balloon wall 43a is formed of an expandable, fibrous material which, when subjected to sufficient inflation pressure, expands to allow minute pores to form in the balloon wall surface 43a. These pores allow fluid to pass through balloon wall surface 43a so that a fluid layer is generated between the porous surface 43a and the membrane 43b, as described above. As shown in FIG. 12, prior to the substantial inflation of fibrous treatment balloon 43, substantially no fluid passes through outer surface 43a of balloon 43. As shown in FIG. 13, upon sufficient inflation of balloon 43, minute pores 7 (shown exaggeratedly in FIG. 13) form in outer surface 43a, thereby providing an exit for the pressurizing fluid as illustrated by arrows in FIGS. 12 and 13. Pores 7 serve to allow a fluid layer to be created between wall surface 43a and membrane 43b.

The feature of the invention described in the preceding two paragraphs provides a fluid layer which aids in removing membrane 43b from the outer surface 43a of treatment balloon 43. Once membrane 43b is released from outer wall surface 43a, the pressure exerted by treatment balloon 43 is preferably sufficient to permanently place membrane 43b onto artery wall surface 2a and/or lesion 5. However, according to a particular preferred feature of the invention, a medication is provided on the surface of membrane 43b prior to its affixation to wall surface 43a which serves to provide membrane 43b and/or artery wall 2a with a "sticky" or adhesive-like property so that membrane 43b adheres or attaches to artery wall surface 2a and/or lesion 5 and remains substantially permanently affixed to the lesion and/or wall surface of a treatment site. An example of a useful medication for this purpose is fibronectin. This medication is preferably dispensed in accordance with a further feature of the invention which will now be described with reference to FIGS. 3 and 6.

Figure 3:
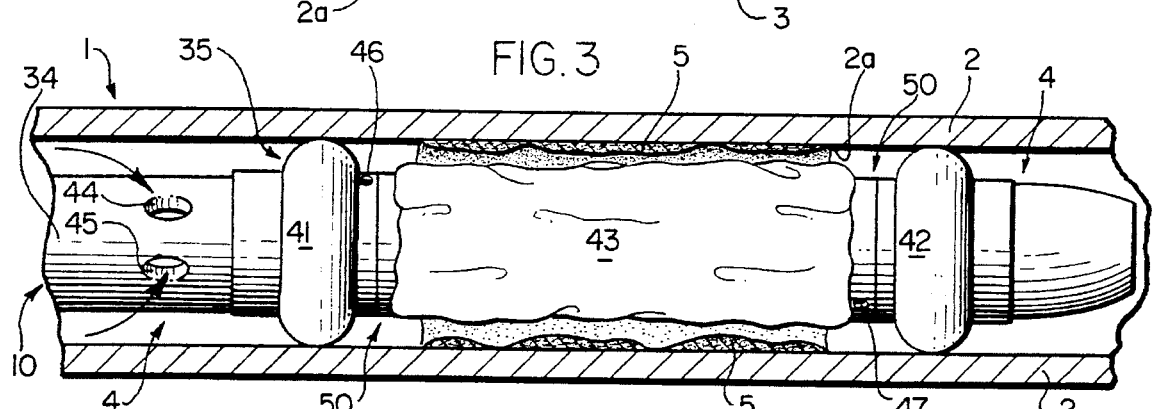
FIG. 3 shows the artery of FIG. 2 wherein an embodiment of the catheter tip of the present invention has been inserted at the blood vessel at the area of the lesion and the spaced chamber balloons are in an inflated state.

According to the feature of the invention which dispenses medication into chamber 50 created by inflated, spaced chamber balloons 41, 42 as shown in FIG. 3, catheter tip 35 is provided with means for providing fluids to and removing fluids from (i.e., rinsing and flushing) chamber 50. Conduit 111 located in catheter wall 107 serves to dispense a saline solution or other medication into chamber 50 through at least one opening 46. For example, conduit 111 may dispense a medication comprising fibronectin in order to aid in the adherence of membrane 43b to artery wall surface 2a and/or lesion 5. Conduit 114 located in catheter wall 107 serves to drain or evacuate liquid, e.g., blood or medication, from chamber 50 through at least one opening 47. Conduits 111 and 114 allow for rinsing and flushing of chamber 50. To avoid the contact of air with the vessel wall, the conduits 111 and 114 (as well as conduit 113 for the treatment balloon 43) can be pre-filled with fluid (e.g., solution, medication, liquid or slurry).

Referring to FIG. 6, to inflate chamber balloons 41, 42 and treatment balloon 43, catheter tip 35 is preferably provided with conduits to supply a pressurizing fluid or medium to balloons 41, 42 and 43. For this purpose, catheter tip 35 preferably utilizes a conduit 112, located in catheter wall 107, for supplying a pressurizing fluid to the spaced chamber balloons 41, 42. Similarly, catheter tip 35 utilizes a conduit 113, located in catheter wall 107, for supplying a pressurizing fluid to treatment balloon 43.

FIG. 7, a cross section view of catheter tip 35 taken along lines 7—7 in FIG. 6, further illustrates the above-described conduit system. Conduit 111, which is located in catheter wall 107, supplies medication to chamber 50. Conduit 114 is also located in catheter wall 107 and serves to drain liquid from the chamber; however, conduit 114 could easily be adapted for supplying liquid to chamber 50. Also located in catheter wall 107 are (a) conduit 112 through which a pressurizing fluid may be supplied to and removed from chamber balloons 41, 42 and (b) conduit 113 through which a pressurizing fluid may be supplied to and removed from treatment balloon 43. Removal of a fluid may be accomplished by suctioning via the conduits.

It should be noted that, although in the embodiment illustrated in FIGS. 6–9, the conduits 111, 112, 113 and 114 are shown in catheter wall 107, such conduits may be situated at any location on catheter 35 so long as the conduits do not hinder the flow of body fluid (e.g., blood). For example, the conduits may alternatively be located along the surface of catheter wall 107, which forms lumen 106, and extend along the length of catheter shaft 34. To avoid clot formation on the surfaces of conduits 111–114 (and other surfaces of the catheter, including the walls forming lumen 106), the catheter surfaces are preferably smooth in texture and rendered nonthrombotic by the application of an anti-clotting medication, e.g., heparin.

Referring to FIG. 10, in one embodiment, inlet 95 is connected with conduit 113 for inflation of treatment balloon 43; inlet 96 is connected with conduit 111 for flushing of chamber 50; inlet 97 is connected with conduit 112 for inflation of chamber balloons 41, 42; inlet 98 is connected with inner lumen 106; and inlet 99 is connected with conduit 114 for evacuation of chamber 50.

Referring again to FIG. 6, the catheter tip 35 also preferably permits the passage of blood from the proximal side to the distal side of catheter tip 35 when chamber balloons 41, 42 are inflated. In FIG. 6, the direction of blood flow is indicated by the arrow "B" at the right side of the figure. For this purpose, one or more inlets, such as inlets 44 and 45, are preferably provided in the catheter shaft 34 or the catheter tip 35 adjacent (and proximal) to inflatable balloon 41. Blood, also designated by arrow "B" at the left side of the figure, enters inlets 44, 45 and flows into lumen 106 at the proximal side of catheter tip 35. The blood then flows downstream in the interior of lumen 106 to the distal side of catheter tip 35 where it exits lumen 106. It is important to have the blood flow only in the direction of arrow "B". In order to assure that the blood flows in this direction, a unidirectional flap or valve 60 may be placed in the lumen just proximal to inlets 44 and 45, as shown in FIGS. 8 and 9. Valve 60 is adapted to be closed in typical circumstances when blood or fluid travels in direction of arrow B in FIGS. 8 and 9, preventing blood or fluid to travel in a direction opposite that of arrow B. The flap wall 61 is an elastic which is adapted to be stretched open as required.

Permitting the blood to flow to the distal side of catheter tip 35 permits the blood to supply oxygen and other nutrients to tissue located distal to catheter tip 35. It is appreciated that additional blood may be supplied from outside of the catheter 10 (shown in FIG. 10) through a lumen in the catheter shaft 34 if the tissue distal to catheter tip 35 becomes ischemic during the procedure. In this situation valve 60 is opened and inlets 44, 45, 108 and 109 close due to the change in the pressure gradient.

FIG. 8 shows, in greater detail, a cross section view (corresponding to the cross section indicated by lines 8—8 in FIG. 7) of the embodiment of the catheter illustrated in FIGS. 6–9 which is located in an artery previously treated by, for example, balloon angioplasty. Referring to FIG. 8, blood flows (in the direction indicated by the arrows "B") inside an artery illustrated by artery wall 2. Catheter tip 35 comprises inflatable chamber balloons 41, 42 and inflatable treatment balloon 43. Chamber balloons 41, 42 are shown in an inflated state in FIG. 8, thereby defining chamber 50. As illustrated in FIG. 8, chamber 50 is oriented generally to be positioned at a site along an artery wall 2 where lesion 5 is located. Chamber 50 permits treatment of lesion 5 without interference from flowing blood. Chamber balloons 41, 42 may have any desired inflated length (as measured along the length of artery wall 2) so long as this length is sufficient to substantially prevent the passage of blood and other liquids into or out of chamber 50 when chamber balloons 41, 42 are in an inflated state. Chamber balloons 41, 42 may, by way of example, each have a length of about 1.5 mm when in an inflated state. Further, although chamber balloons 41, 42 are shown as having the same size in the drawing, this need not be the case. Similarly, while two spaced chamber balloons 41, 42 have been shown, it is appreciated that, if desired, additional chamber balloons, as well as additional treatment balloons, could be utilized.

Treatment balloon 43, shown in an inflated state in FIG. 8, preferably has an inflated length (as measured along the length of artery wall 2) sufficient to apply a membrane which covers not only the entire surface of lesion 5 but also covers some portion of the artery wall surface 2a beyond lesion 5. Such extended coverage will help membrane 43b to adhere to the afflicted portion of the artery. Preferably, various sizes of treatment balloon 43 are available to the user of the catheter depending upon the length of the afflicted portion of artery 1. However, treatment balloon 43 may have an inflated length, by way of example only, of about 10 mm as measured along the length of artery wall 2. The total length of chamber 50 in which treatment balloon 43 is located may be, by way of example only, about 13.5 mm, as measured along the length of artery wall 2. Nevertheless, it should be clearly understood that the dimensions of balloons useful in conjunction with the inventive catheter tip are variable and dependent upon the body vessel or cavity in which the catheter is utilized.

As described above, to permit blood to flow to tissue located on the distal side of catheter tip 35, there is provided inlets 44, 45, 108 and 109 which allow blood to enter interior lumen 106, as indicated by the arrows "B" in FIGS. 8 and 9. Inlets 44, 45, 108, 109 preferably each have a diameter of about 0.25–0.50 mm. Lumen 106 has a diameter which allows for sufficient passage of body fluid, e.g., blood, to the distal side of catheter tip 35. Therefore, the preferred size of lumen 106 varies depending upon the body vessel in which the catheter is utilized. By way of example only, for use in a blood vessel, lumen 106 may have a diameter of about 2 mm. Catheter wall 107 preferably has a width of about 0.5 mm. Conduits 111, 112, 113, 114 each may have a diameter, for example, of about 0.25 mm. Blood exits catheter tip 35 on the distal side of chamber balloon 42 to supply blood to tissue distal to catheter tip 35.

FIG. 9 shows a different longitudinal cross section (corresponding to the cross section indicated by lines 9—9 in FIG. 7) of the catheter tip illustrated in FIGS. 6–8. Catheter tip 35 is shown within an artery 1 having artery wall 2. Catheter tip 35 has inflatable chamber balloons 41, 42 and inflatable treatment balloon 43, all of which are shown in an inflated state, thereby defining chamber 50. Inlets 108 and 109 (similar to inlets 44, 45 in FIG. 8) allow blood to flow into lumen 106 of the catheter defined by catheter wall 107. Blood exits lumen 106 distal to chamber balloon 42. FIG. 9 also illustrates the conduit system including conduits 111, 114, described above, which preferably provide means for rinsing and flushing chamber 50.

A method will now be described for using the catheter of the present invention in a procedure for preventing the restenosis of a human blood vessel after a PTA, PTCA or atherectomy procedure. It should again be noted that a catheter in accordance with the present invention is not limited to use in a blood vessel, and the inventive catheter may be used to treat any body vessel or cavity.

Referring to FIG. 3, and for illustrative purposes only, the inventive procedure for preventing restenosis of a post PTA/PTCA artery commences with the insertion of a catheter 10 having catheter tip 35 at or near the end of a flexible catheter shaft 34, into the afflicted area of artery 1. Specifically, catheter tip 35 is placed at the site of previously treated lesion 5.

Chamber balloons 41, 42 are inflated to isolate the portion of artery wall 2 having plaque 3 attached thereto in the form of lesion 5. Inflation of chamber balloons 41, 42 creates chamber 50, which is positioned to be oriented about the lesion 5.

Blood inlets 44, 45, 108 and 109 permit blood from artery 1 to flow into catheter lumen 106 (shown in FIGS. 8–9). Blood flows through catheter lumen 106 to the distal side of chamber balloon 42 and exits catheter tip 35 whereby the blood continues to supply nutrients to that portion of the artery 1 distal to catheter tip 35.

After inflation of chamber balloons 41 and 42 to form chamber 50, blood and other fluid, if any, in chamber 50 is evacuated through catheter outlet 47 and conduit 114. Following fluid evacuation of chamber 50, chamber 50 preferably is rinsed and flushed one or more times, as may be required, with a medication, for example, a mixture of heparin, glycosaminoglycan, a smooth muscle cell proliferation inhibitor, and fibronectin in a cocktail form. Fibronectin is preferably utilized in order to provide artery wall 2 with an adhesive-like property so that membrane 43b will attach or adhere to artery wall 2 upon sufficient pressure contact between treatment balloon wall 43a and artery wall 2. The fluid medication is supplied via conduit 111 and inlet 46 into chamber 50.

FIG. 3 shows treatment balloon 43 at this stage of the procedure in a deflated state, however, as will be described below, treatment balloon 43 will be inflated to place a membrane on the inner surface of artery wall 2 and/or lesion 5.

Figure 4:
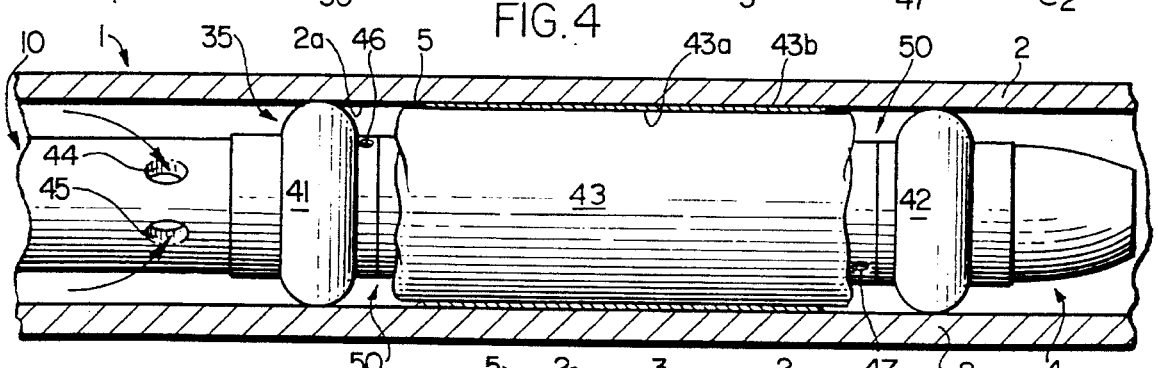
FIG. 4 shows the embodiment of the catheter tip of FIG. 3 wherein the treatment balloon also is in an inflated state.

FIG. 4 is illustrative of the remaining steps of the inventive method for treating the post PTA/PTCA artery wall 2. Following rinsing and flushing of chamber 50, treatment balloon 43, which preferably has a porous outer wall 43a, is inflated with a liquid and/or gas fluid, as shown in FIG. 4. Located on the exterior balloon surface 43a is membrane 43b which, in this embodiment, was already located on the catheter tip prior to insertion of catheter 10 into a body to be treated.

According to a preferred method, once the porous treatment balloon 43 is inflated with a pressurizing fluid and contacts the artery wall surface 2a, an additional amount of pressurizing fluid, e.g., heparin or glycosaminoglycan, is supplied to the treatment balloon 43. The procedure is optionally paused prior to supplying the additional pressurizing fluid. By increasing the pressure in the inflated treatment balloon 43, the pressurizing fluid exits the pores of the porous balloon 43, thereby forming a fluid layer on the balloon wall surface 43a to aid in the release of membrane 43b from balloon surface 43a. Due to the pressure exerted by the fluid layer on membrane 43b and because artery wall surface 2a has been pre-treated to have an adhesive-like surface, membrane 43b contacts and attaches to artery wall surface 2a. Membrane 43b will remain substantially fixed to artery wall surface 2a and/or lesion 5 upon deflation of balloon 43. Membrane 43b preferably covers the length of lesion 5 and at least a portion of artery wall surface 2a.

While, in this instance, membrane 43b is transferred to the vessel and/or lesion surface, it is appreciated a slurry or other fluid, such as previously discussed, could be used to generate a membrane which then would solidify on the lesion or vessel wall surface, for example by the addition of a further treatment or a temperature change.

After membrane 43b is attached to artery wall 2, treatment balloon 43 is deflated by draining the pressurizing fluid from balloon 43 via conduit 113 (shown in FIG. 8). Chamber 50 again is preferably rinsed and flushed, followed by deflation of chamber balloons 41, 42 via conduit 112 (shown in FIG. 8). The catheter shaft 34 and catheter tip 35 are thereafter removed from the artery to restore full blood flow.

Figure 5:
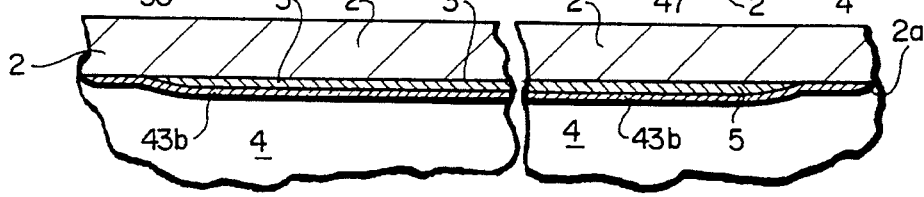
FIG. 5 shows a fragmentary, longitudinal cross section view of an artery wall wherein a membrane has been transferred from the treatment balloon of the catheter of the present invention and deposited on the vessel wall at the location of the lesion.
Figure 14A:
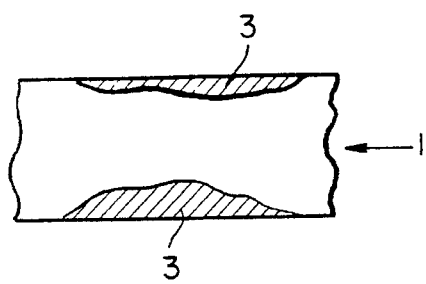
FIG. 14(a) shows a fragmentary, longitudinal cross section view of an artery having a lesion thereon.
Figure 14B:
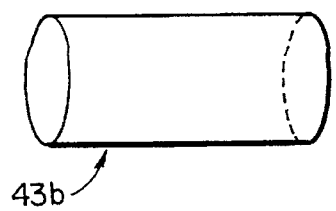
FIG. 14(b) shows an embodiment of a membrane adapted for the treatment thereof.
Figure 15A:
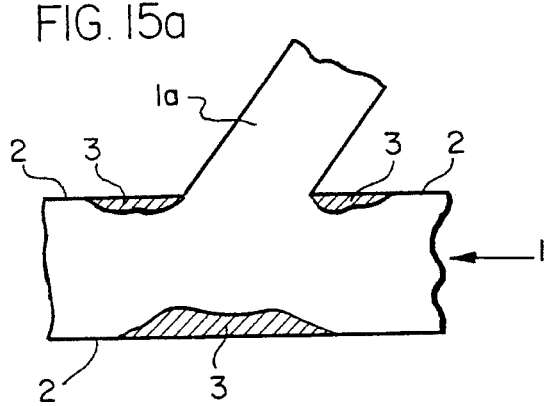
FIGS. 15(a) and (b) respectively show a fragmentary, longitudinal cross section view of an artery having lesions thereon and an embodiment of a membrane adapted for the treatment thereof.
Figure 15B:
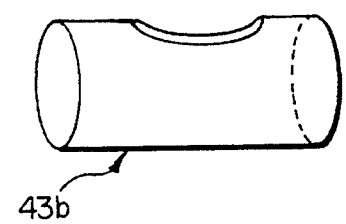
Figure 16A:
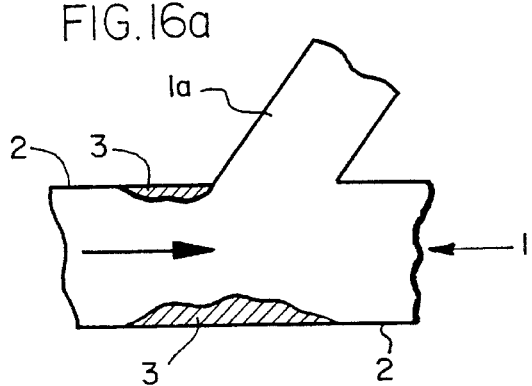
FIGS. 16(a) and (b) respectively show a fragmentary, longitudinal cross section view of an artery having lesions thereon and an embodiment of a membrane adapted for the treatment thereof; and, FIGS. 17(a) and (b) respectively show a fragmentary, longitudinal cross section view of an artery having lesions thereon and an embodiment of a membrane adapted for the treatment thereof.
Figure 16B:
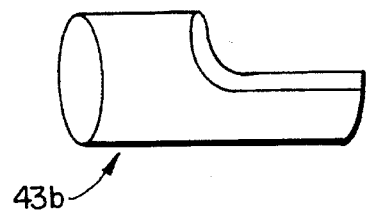
Figure 17A:
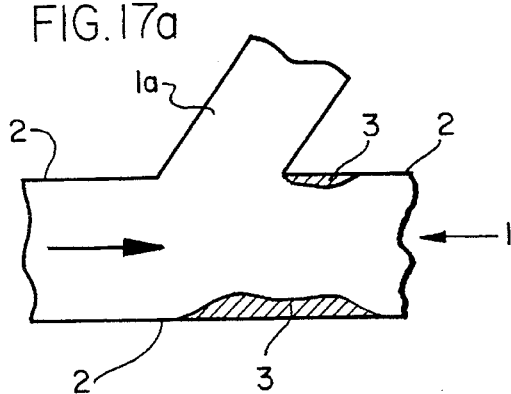
Figure 17B:
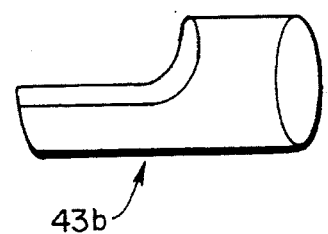

FIG. 5 illustrates a partial cross section of an artery which has been treated in accordance with the inventive method. Located on the surface 2a of artery wall 2 is plaque 3 remaining after a balloon angioplasty procedure which was performed prior to performing the inventive procedure.

Membrane 43b is affixed to plaque 3 for the length of lesion 5. Preferably, membrane 43b also adheres to an exposed portion of artery wall surface 2a. Membrane 43b protects plaque 3 and artery wall 2 and serves to obviate the problems heretofore discussed, e.g., collection of thrombotic particles, which may occur when blood flows through the lumen 4 of the blood vessel. Membrane 43b serves to preclude blood from contacting (a) plaque 3 and (b) the inner layers of artery wall 2, thereby serving to prevent restenosis of the artery.

While one or more embodiments of the invention have been herein illustrated and described in detail, it will be understood that modifications and variations thereof may be effected without departing from the spirit of the invention and the scope of the appended claims.

What is claimed is:

1. A catheter device for treating a living body having a treatable surface, comprising:

(a) an elongated flexible shaft having a proximal end and a distal end;

(b) a catheter tip having a proximal end and a distal end, said proximal catheter tip end being joined to said catheter distal shaft end;

(c) said tip comprising at least two spaced, inflatable cheer balloons which, when inflated in said body serve to form a treatment site in the space formed between said chamber balloons;

(d) an inflatable treatment balloon consisting essentially of an inflatable, porous material, said treatment balloon being disposed on said tip and positioned between said spaced cheer balloons;

(e) means associated with said inflatable treatment balloon for treating said treatment site when said chamber and treatment balloons are inflated, said treatment means comprising a material having a structure substantially similar to the physiological structure of said surface of said body;

(f) flushing means for (i) supplying material to and/or (ii) removing fluid and/or debris from said chamber; and, (g) means for allowing flow of body fluid from the proximal side to the distal side of said catheter tip when any of said balloons is in an inflated state.

2. A device as recited in claim 1 wherein:

said treatment means comprises means for providing a material to said body which is suitable for treatment and/or prophylaxis of pathological conditions or functions of said living body.

3. A device as recited in claim 1 wherein:

said treatment means comprises means for providing endothelial cells to said living body.

4. A device as recited in claim 1 wherein:

said treatment means comprises means for providing a slurry to said living body.

5. A device as recited in claim 1 and further comprising a conduit located in said flexible shaft.

6. A device as recited in claim 1 wherein:

(1) said surface comprises endothelial cells, and (2) said treatment means comprises material substantially similar to said endothelial cells.

7. A device as recited in claim 1 wherein:

said treatment means comprises a material selected from the group consisting of endothelial cells, homologues of endothelial cells, inverted homologues of endothelial cells, heterologues of endothelial cells, inverted heterologues of endothelial cells, autologues of endothelial cells, and inverted autologues of endothelial cells.

8. A device as recited in claim 1 wherein said flushing means comprises means for supplying a medication to said chamber.

9. A catheter device for treating a living body having a treatable surface, comprising:

(a) an elongated flexible shaft having a proximal end and a distal end;

(b) a catheter tip having a proximal end and a distal end, said proximal catheter tip end being joined to said catheter distal shaft end;

(c) said tip comprising at least two spaced, inflatable chamber balloons adapted to form a space between said chamber balloons when said chamber balloons are inflated;

(d) an inflatable treatment balloon having an exterior wall surface, said treatment balloon consisting essentially of an inflatable, porous material and being disposed on said tip between said spaced chamber balloons;

(e) a coating membrane releasably disposed on said exterior wall surface of said treatment balloon, said membrane releasable from said treatment balloon and maintainable on a body wall surface, said membrane comprising a material having a structure substantially similar to the physiological structure of said surface of said body;

(f) means for displacing said membrane from the exterior wall surface of said treatment balloon when said catheter tip is inserted in a living body and said treatment balloon is inflated;

(g) flushing means for (i) supplying material to and/or (ii) removing fluid and/or debris from said chamber; and, (h) means for allowing flow of body fluid from the proximal side to the distal side of said catheter tip when any of said balloons is in an inflated state.

10. A device as recited in claim 9 wherein:

said releasable coating membrane comprises a material which is suitable for treatment and/or prophylaxis of pathological conditions or functions of said living body.

11. A device as recited in claim 9 wherein:

said catheter comprises means for treating a body vessel or cavity;

said vessel or cavity has a wall surface; and said membrane comprises a material which is substantially similar to the material forming the wall surface.

12. A device as recited in claim 9 wherein:

said membrane comprises human endothelial cells.

13. A device as recited in claim 9 wherein:

said membrane comprises an autologue of endothelial cells.

14. A device as recited in claim 9 wherein:

said membrane comprises a heterologue of endothelial cells.

15. A device as recited in claim 9 wherein:

said membrane comprises denaturalized endothelial cells.

16. A device as recited in claim 9 wherein said means for displacing the membrane from the exterior wall surface of said treatment balloon comprises:

means for creating pressure differences to form a fluid flow through said porous balloon.

17. A device as recited in claim 9 and further comprising:

means for removing said coating membrane from the exterior wall surface of said treatment balloon.

18. A device as recited in claim 9 wherein:

(1) said surface comprises endothelial cells, and (2) said membrane comprises a material substantially similar to said endothelial cells.

19. A device as recited in claim 9 wherein:

said membrane comprises a material selected from the group consisting of endothelial cells, homologues of endothelial cells, inverted homologues of endothelial cells, heterologues of endothelial cells, inverted heterologues of endothelial cells, autologues of endothelial cells, and inverted autologues of endothelial cells.

20. A device as recited in claim 9 wherein said flushing means comprises means for supplying a medication to said chamber.

21. A method for preventing stenosis in a body vessel or cavity having an inner wall surface, said method comprising the steps of:

(a) inserting a catheter tip having a proximal end and a distal end in a desired location along said inner wall surface;

(b) providing said tip with at least two spaced inflatable chamber balloons and at least one treatment balloon located between said chamber balloons, said treatment balloon having an exterior wall surface and consisting essentially of an inflatable, porous material;

(c) inflating said spaced chamber balloons to isolate a portion of said vessel or cavity between said spaced chamber balloons;

(d) (i) supplying material to and/or (ii) removing fluid and/or debris from said isolated portion;

(e) providing a treatment to said isolated portion of said vessel or cavity, said treatment having a structure substantially similar to the physiological structure of said surface of said vessel or cavity;

(f) inflating said treatment balloon so as to provide said treatment to said isolated portion of said body vessel or cavity; and, (g) allowing flow of body fluid from the proximal side to the distal side of said catheter tip when any of said balloons is in an inflated state.

22. A method as recited in claim 21 wherein:

said treatment comprises a material suitable for the treatment or prophylaxis of pathological conditions or functions of the surface of the walls of said vessel or cavity.

23. A method as recited in claim 21 wherein:

said treatment comprises a slurry which includes endothelial cells.

24. A method as recited in claim 21, further comprising:

applying pressure with said treatment balloon on said body vessel or cavity sufficient to maintain said treatment on said isolated portion of said body vessel or cavity.

25. A method as recited in claim 21 wherein:

(1) said surface comprises endothelial cells, and (2) said treatment comprises a material substantially similar to said endothelial cells.

26. A method as recited in claim 21 wherein:

said treatment comprises a material selected from the group consisting of endothelial cells, homologues of endothelial cells, inverted homologues of endothelial cells, heterologues of endothelial cells, inverted heterologues of endothelial cells, autologues of endothelial cells, and inverted autologues of endothelial cells.

27. A method as recited in claim 21, and further comprising:

supplying a medication comprising a smooth muscle cell proliferation inhibitor to said isolated portion of said vessel or cavity prior to and after inflating said treatment balloon.

28. A method as recited in claim 21, and further comprising:

supplying a medication comprising an adhesive agent to said isolated portion of said vessel or cavity.

29. A method as recited in claim 21 wherein said vessel or cavity is a blood vessel.

30. A method for preventing stenosis in a body vessel or cavity having an inner wall surface, said method comprising the steps of:

(a) inserting a catheter tip having a proximal end and a distal end to a desired location along said inner wall surface;

(b) providing said tip with at least two spaced inflatable chamber balloons;

(c) providing said tip with an inflatable treatment balloon having an exterior wall surface, said treatment balloon being disposed on said tip between said spaced chamber balloons and consisting essentially of an inflatable, porous material;

(d) providing, on the exterior wall surface of said treatment balloon, a releasable membrane comprising a material having a structure substantially similar to the physiological structure of said surface of said vessel or cavity;

(e) inflating said spaced chamber balloons to isolate a portion of said vessel or cavity between said spaced chamber balloons;

(f) (i) supplying material to and/or (ii) removing fluid and/or debris from said isolated portion;

(g) inflating said treatment balloon and displacing said membrane from the surface of said treatment balloon onto said body wall surface;

(h) maintaining said membrane on said inner wall surface of said body vessel or cavity; and, (i) allowing flow of body fluid from the proximal side to the distal side of said catheter tip when any of said balloons is in an inflated state.

31. A method as recited in claim 21 or 30, and further comprising:

draining body fluid from said isolated portion of said vessel or cavity after inflating said chamber balloons.

32. A method as recited in claim 30 wherein:

said coating membrane is formed of a material suitable for the treatment or prophylaxis of pathological conditions or functions of the surface of the walls of said vessel or cavity.

33. A method as recited in claim 30 wherein:

said membrane comprises endothelial cells.

34. A method as recited in claim 30 and further comprising:

providing said treatment balloon with a porous balloon wall; and directing a fluid through said porous wall whereby said membrane is released from said exterior wall surface of said treatment balloon and displaced on to said inner wall body vessel or cavity surface.

35. A method as recited in claim 30, and further comprising:

treating said isolated portion of said vessel or cavity with medication after displacing said coating membrane to the inner wall surface of said vessel or cavity.

36. A method as recited in claims 21 or 30 wherein said vessel or cavity is a blood vessel, said method further comprising:

performing an angioplasty procedure prior to inserting said catheter tip into said blood vessel.

37. A method as recited in claims 21 or 30 wherein said vessel or cavity is a blood vessel, said method further comprising:

performing an atherectomy procedure prior to inserting said catheter tip into said blood vessel.

38. A method as recited in claim 30, further comprising:

releasing said membrane from said treatment balloon onto said isolated portion while maintaining pressure by said treatment balloon on said membrane and inner wall surface.

39. A method as recited in claim 30 wherein:
(1) said surface comprises endothelial cells, and (2) said membrane comprises a material substantially similar to said endothelial cells.

40. A method as recited in claim 30 wherein:
said membrane comprises a material selected from the group consisting of endothelial cells, homologues of endothelial cells, inverted homologues of endothelial cells, heterologues of endothelial cells, inverted heterologues of endothelial cells, autologues of endothelial cells, and inverted autologues of endothelial cells.

41. A method as recited in claim 30 wherein said vessel or cavity is a blood vessel.

42. A method as recited in claims 21 or 30, comprising:
supplying medication to said isolated portion of said vessel or cavity prior to inflating said treatment balloon.

43. A method as recited in claim 42 wherein:
said medication comprises a smooth muscle cell proliferation inhibitor.

44. A method as recited in claim 42 wherein:
said medication comprises an adhesive agent or material.

\* \* \* \* \*

UNITED STATES PATENT AND TRADEMARK OFFICE
CERTIFICATE OF CORRECTION

PATENT NO.   :   5,599,307

DATED        :   February 4, 1997

INVENTOR(S)  :   Bacher et al.

It is certified that error appears in the above-identified patent and that said Letters Patent is hereby corrected as shown below:

Col. 5, line 26, delete "ill" and insert --in-- therefor.

Col. 15, line 1, delete "cheer" and insert --chamber-- therefor; and

Col. 15, line 8, delete "cheer" and insert --chamber-- therefor.

Signed and Sealed this

Fifteenth Day of July, 1997

Attest:

BRUCE LEHMAN

*Attesting Officer*   *Commissioner of Patents and Trademarks*